United States Patent
Roldan et al.

(10) Patent No.: US 11,154,369 B2
(45) Date of Patent: Oct. 26, 2021

(54) ENVIRONMENTAL MAPPING FOR ROBOTIC ASSISTED SURGERY

(71) Applicant: THINK SURGICAL, INC., Fremont, CA (US)

(72) Inventors: Jay Roldan, Fremont, CA (US); Randall Hanson, Fremont, CA (US)

(73) Assignee: THINK SURGICAL, INC., Fremont, CA (US)

(*) Notice: Subject to any disclaimer, the term of this patent is extended or adjusted under 35 U.S.C. 154(b) by 269 days.

(21) Appl. No.: 16/250,341

(22) Filed: Jan. 17, 2019

(65) Prior Publication Data
US 2019/0223962 A1 Jul. 25, 2019

Related U.S. Application Data

(60) Provisional application No. 62/621,307, filed on Jan. 24, 2018.

(51) Int. Cl.
*A61B 34/30* (2016.01)
*A61B 17/56* (2006.01)
(Continued)

(52) U.S. Cl.
CPC .............. *A61B 34/30* (2016.02); *A61B 17/56* (2013.01); *A61B 34/10* (2016.02); *A61B 34/20* (2016.02);
(Continued)

(58) Field of Classification Search
CPC ......... A61B 34/30; A61B 34/10; A61B 34/20; A61B 17/56; A61B 2034/2051; A61B 2034/2068; A61B 17/16; A61B 2034/2059; A61B 2034/102; A61B 2017/564; A61B 2034/104; A61B 2034/105;
(Continued)

(56) References Cited

U.S. PATENT DOCUMENTS 5,086,401 A 2/1992 Glassman et al.
5,872,894 A 2/1999 Watanabe et al.
(Continued)

FOREIGN PATENT DOCUMENTS

WO 2017115235 A1 7/2017

OTHER PUBLICATIONS

Bobrow, J.E. et al., "Time-Optimal Control of Robotic Manipulators Along Specified Paths", The International Journal of Robotics Research, Fall 1985, pp. 3-17, vol. 4, No. 3, © 1985 Massachusetts Institute of Technology.
(Continued)

*Primary Examiner* — Basil T. Jos
(74) *Attorney, Agent, or Firm* — Blue Filament Law PLLC

(57) ABSTRACT

A system and method of use thereof are provided for dynamically generating an environmental map for use in robotic assisted surgery. The generated environmental map is used to plan a recovery tool path that an end-effector tool can safely and efficiently follow to re-position the tool back to a cutting position following the displacement of the tool from the cutting position. Additionally, the environmental map is used to update a virtual representation of a bone to provide a user with visual feedback as to the progression of the end-effector tool as the tool removes material from the bone during a surgical procedure.

19 Claims, 4 Drawing Sheets

(51) Int. Cl.
*A61B 34/10* (2016.01)
*A61B 34/20* (2016.01)
*A61B 90/00* (2016.01)
*A61B 34/00* (2016.01)
*A61B 17/16* (2006.01)

(52) U.S. Cl.
CPC ......... *A61B 17/16* (2013.01); *A61B 2017/564* (2013.01); *A61B 2034/102* (2016.02); *A61B 2034/104* (2016.02); *A61B 2034/105* (2016.02); *A61B 2034/107* (2016.02); *A61B 2034/2051* (2016.02); *A61B 2034/2055* (2016.02); *A61B 2034/2059* (2016.02); *A61B 2034/2068* (2016.02); *A61B 2034/252* (2016.02); *A61B 2034/743* (2016.02); *A61B 2034/744* (2016.02); *A61B 2090/3937* (2016.02); *A61B 2090/3983* (2016.02)

(58) Field of Classification Search
CPC .... A61B 2090/3983; A61B 2034/2055; A61B 2034/252; A61B 2034/743; A61B 2034/744; A61B 2090/3937; A61B 2034/107
See application file for complete search history.

(56) References Cited

U.S. PATENT DOCUMENTS

| | | | |
|---|---|---|---|
| 6,033,415 | A | 3/2000 | Mittelstadt et al. |
| 6,061,644 | A | 5/2000 | Leis |
| 6,430,434 | B1 | 8/2002 | Mittelstadt |
| 7,043,961 | B2 | 5/2006 | Pandey et al. |
| 8,010,177 | B2 | 8/2011 | Csavoy et al. |
| 8,036,441 | B2 | 10/2011 | Frank et al. |
| 8,287,522 | B2 | 10/2012 | Moses et al. |
| 9,592,606 | B2 | 3/2017 | Rümping et al. |
| 9,675,421 | B2 | 6/2017 | Hourtash et al. |
| 2016/0345929 | A1 | 12/2016 | Azizian et al. |
| 2017/0245945 | A1 | 8/2017 | Zuhars et al. |
| 2018/0014888 | A1 | 1/2018 | Bonny et al. |
| 2018/0185100 | A1* | 7/2018 | Weinstein .............. A61B 34/20 |

OTHER PUBLICATIONS

Harmon, L. et al., "3D Laser Scanning for Image-Guided Neurosurgery", AAAI Technical Report SS-94-05, 1994, pp. 106-109, © 1994 AAAI.

* cited by examiner

ENVIRONMENTAL MAPPING FOR ROBOTIC ASSISTED SURGERY

RELATED APPLICATIONS

This application claims priority benefit of U.S. Provisional Application Ser. No. 62/621,307 filed 24 Jan. 2018; the contents of which are hereby incorporated by reference.

FIELD OF THE INVENTION

The present invention generally relates to the field of robotic-assisted orthopedic surgery, and more particularly to a system and method for dynamically generating an environmental mapping for use in robotic assisted surgery.

BACKGROUND OF THE INVENTION

Robotic surgery is an expanding field having applications in orthopedics, neurology, oncology, and soft-tissue procedures. In the field of orthopedics, robotic surgical systems generally aid in the planning and execution of a bone procedure to repair and replace a damaged joint. The TSOLUTION ONE® Surgical System (THINK Surgical, Inc., Fremont, Calif.) is one such system that aids in the planning and execution of total hip arthroplasty (THA) and total knee arthroplasty (TKA). The TSOLUTION ONE® Surgical System includes: a pre-operative planning software program to generate a surgical plan; and an autonomous surgical robot that precisely mills the bone to receive an implant according to the plan. In more detail, with reference to FIG. 1A, a user plans the placement of an implant model IM (e.g., a computer aided design (CAD) file of the implant) relative to a three-dimensionally generated bone model BM of the patient's bone to designate the best fit, fill, and alignment for the implant in each patient case. Once completed, the plan is saved and transferred to the robot for execution intra-operatively. In the operating room (OR), the plan is registered to the bone and the surgical robot controls an end-effector tool to mill the bone according to the plan. More specifically, as shown in FIG. 1B, the end-effector tool is manipulated based on a cut-file having cutting parameters. The cutting parameters includes a tool path 10, among other parameters (e.g., feed-rates, spindle speed), that defines the motion for the end-effector tool to accurately modify the bone B according to the planned implant placement.

However, the robot only knows the POSE of the registered bone and the tool path 10 on which to control the end-effector tool. The robot, without any other sensors (e.g., laser scanner), lacks information about the environment including the presence or absence of obstacles (e.g., clinical staff, patient's anatomy) in the robot's workspace. Therefore, an obstacle may unintentionally encounter the end-effectors toolpath.

One particular situation where the end-effector tool may encounter an obstacle is during a tool path recovery procedure. Whenever a procedure is paused for a safety reason, the surgical team needs to investigate the problem to ensure the end-effector tool is cutting as intended and the patient is safe. To obtain a better view of the surgical site, the surgical team manually displaces (e.g., guides, removes) the end-effector tool away from the surgical site to inspect the problem. Once the problem is alleviated or addressed, the user may resume the procedure. To resume the procedure, the position of the end-effector tool needs to be recovered, meaning the end-effector tool needs to be re-positioned back to, or near, the tools previous cutting position. In one method, the cut-file may include a plurality of checkpoints (20a, 20b, 20c, 20d) positioned along the tool path 10 to recover the position of the end-effector tool back to, or near the tool path 10. As the end-effector tool passes the checkpoints (20a, 20b, 20c, 20d) in the tool path 10, the last checkpoint passed when the procedure was paused may be used as a reference location to re-position the cutter. For example, if the end-effector tool was milling between checkpoints 20c and 20d when the pause occurred, then checkpoint 20c is used as the last checkpoint to recover the position of the end-effector tool.

However, as previously mentioned, the robot has no external information about the environment, including obstacles (e.g., un-cut bone), which may exist between the displaced position of the end-effector tool and the previous cutting position without having external sensors or a model of the environment. Therefore, robot-to-bone collisions while recovering the position of the end-effector tool are possible without manual user assistance, which may pose a risk to the patient and increase the surgical time.

Thus, there is a need in the art for a method to dynamically generate an environmental map for use during robot assisted surgery. There further exists a need to dynamically plan a recovery tool path that an end-effector tool can safely and efficiently follow to re-position the tool back to, or near, a cutting position following the displacement of the tool from the cutting position with the aid of the environmental map.

SUMMARY OF THE INVENTION

A method is provided to dynamically generate an environmental map in a robotic assisted surgery system. The method includes registering a physical surface contour of a bone to the robotic assisted surgical system, and determining a high point on the surface contour. A boundary is defined in the environmental map based on the high point and a plane non-parallel to a longitudinal axis of the bone, and regions are labeled starting at the boundary and away from the bone as free space in the environmental map, as well as regions labeled starting at the boundary and towards the bone as invalid space in the environmental map. The method further includes removing material from a workpiece or the bone by manipulating an end-effector tool with a manipulator arm along a tool path of the robotic surgical system, and dynamically generating the environmental map as material is being removed by labeling the removed material as free space in the environmental map and labeling the non-removed material as invalid space in the environmental map.

A surgical system is provided for performing the computerized method to dynamically generate an environmental map in a robotic assisted surgery system. The system includes a surgical robot with an end effector tool, a computing system having user-peripherals and a monitor for displaying a graphical user interface (GUI), and at least one of a mechanical digitizer or a non-mechanical tracking system.

BRIEF DESCRIPTION OF THE DRAWINGS

The present invention is further detailed with respect to the following drawings that are intended to show certain aspects of the present of invention, but should not be construed as limit on the practice of the invention, wherein:

FIG. 4A depicts a tool removing bone, FIG. 4B depicts a position of the tool when a pause in the procedure occurs, and FIG. 4C depicts the tool displaced from the tool path and a recovery tool path for recovering the position of the tool from the displaced position back to, or near, the previous cutting position as shown in FIG. 4B.

DETAILED DESCRIPTION

Figure 1A:
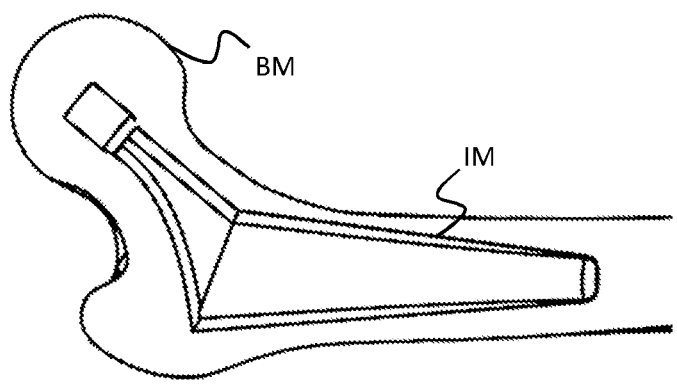
FIG. 1A depicts a planned placement of an implant model relative to a bone model as is known in the prior art.
Figure 1B:
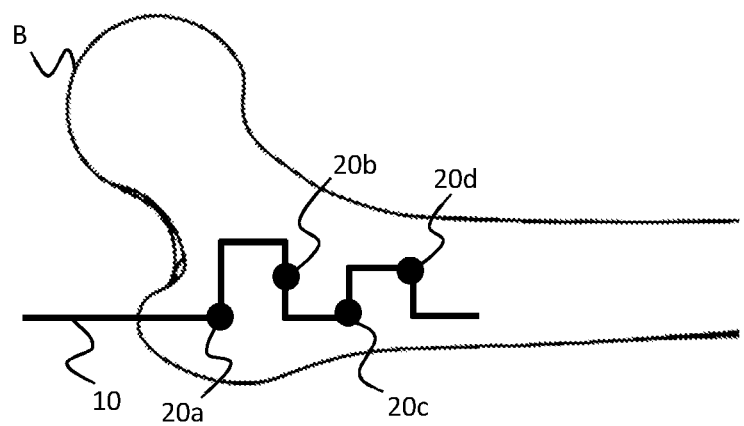
FIG. 1B depicts a tool path having checkpoints for removing bone according to the planned placement as is known in the prior art.

The present invention has utility as a system and method for dynamically generating an environmental map for use in robotic assisted surgery. The system and method are particularly advantageous for generating an environmental map to plan a recovery tool path that an end-effector tool can safely and efficiently follow to re-position the tool back to a cutting position following the displacement of the tool from the cutting position. Additionally, the environmental map may be particularly useful to update a virtual representation of a bone to provide a user with visual feedback as to the progression of the end-effector tool as the tool removes material from the bone.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Further, it should be appreciated that although the systems and methods described herein make reference to the proximal femur bone, the systems and methods may be applied to other bones and joints in the body illustratively including the knee, ankle, elbow, wrist, skull, and spine, as well as revision of initial repair or replacement of any of the aforementioned bones or joints. It should further be appreciated that the systems and methods described herein may be applied to industrial applications, such as the generation of an environmental map for a computer numerical control (CNC) machine that mills inanimate workpieces (e.g., wood, metal).

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "recovery marker" refers to a physical reference marker designed to permit a measurement system, such as a mechanical tracking system, optical tracking system, electro-magnetic tracking system, ultrasound tracking system, and/or an imaging system (e.g., computed tomography (CT), X-ray, fluoroscopy, ultrasound, magnetic resonance imaging (MRI)), to determine at least one of a position or orientation of at least a portion of the reference marker.

As used herein, the term "registration" refers to the determination of the spatial relationship between two or more objects or coordinate systems such as a computer-assist device, a bone, or an image data set of a bone. Illustrative methods of registration known in the art are described in U.S. Pat. Nos. 6,033,415, 8,010,177, 8,036,441, and 8,287,522. "Re-registration" refers to any subsequent registration procedure that occurs after an initial registration and is executed with the use of the recovery markers.

As used herein, the term "end-effector tool" refers to an instrument that is manipulated/guided by an external device (e.g., surgical robot, CNC machine) and interacts with a workpiece (e.g., bone). Illustrative examples of an end-effector tool include a cutter, an end-mill, a burr, a probe, an electrocautery device, a reamer, an impactor, a drill bit, a screw, forceps, scissors, and a saw.

As used herein, the term "real-time" refers to the processing of input data within milliseconds such that calculated values are available within 10 seconds of computational initiation.

Figure 2:
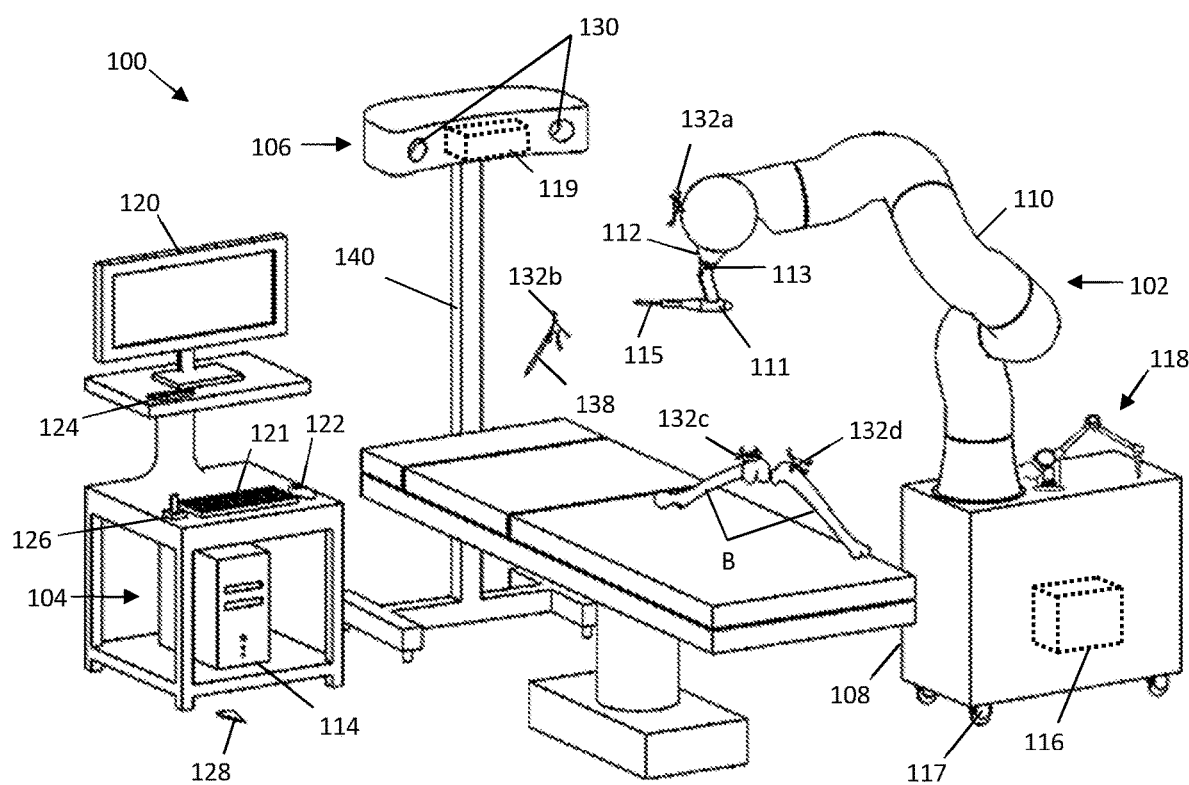
FIG. 2 depicts a surgical system having an environmental map generator software module for dynamically generating an environmental map in accordance with embodiments of the invention.

With reference now to the figures, FIG. 2 depicts an embodiment of a robotic surgical system 100 shown in the context of an operating room (OR). The robotic surgical system 100 is capable of implementing embodiments of the inventive method as described herein. The surgical system 100 generally includes a surgical robot 102, a computing system 104, and includes at least one of a mechanical digitizer 118 or a non-mechanical tracking system 106 (e.g., an optical tracking system, an electro-magnetic tracking system).

The surgical robot 102 may include a movable base 108, a manipulator arm 110 connected to the base 108, an end-effector flange 112 located at a distal end of the manipulator arm 110, and an end-effector assembly 111 removably attached to the flange 112 by way of an end-effector mount/coupler 113. The end-effector assembly 111 holds and/or operates an end-effector tool 115 that interacts with a portion of a patient's anatomy. The base 108 includes a set of wheels 117 to maneuver the base 108, which may be fixed into position using a braking mechanism such as a hydraulic brake. The base 108 may further include an actuator to adjust the height of the manipulator arm 110. The manipulator arm 110 includes various joints and links to manipulate the tool 115 in various degrees of freedom. The joints are illustratively prismatic, revolute, spherical, or a combination thereof.

The computing system 104 generally includes a planning computer 114; a device computer 116; an optional tracking computer 119 if a tracking system 106 is present; and peripheral devices. The planning computer 114, device computer 116, and tracking computer 119, may be separate entities, a single collective unit, or combinations thereof depending on the surgical system. The peripheral devices allow a user to interface with the robotic surgical system 100 and may include: one or more user-interfaces, such as a display or monitor 120 for displaying a graphical user interface (GUI); and user-input mechanisms, such as a keyboard 121, mouse 122, pendent 124, joystick 126, foot pedal 128, or the monitor 120 in some inventive embodiments have touchscreen capabilities.

The planning computer 114 contains hardware (e.g., processors, controllers, and memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan includes operational data for modifying a volume of tissue that is defined relative to the anatomy, such as a set of points in a cut-file to autonomously modify the volume of bone, a set of virtual boundaries defined to haptically constrain a tool within the defined boundaries to modify the bone, a set of planes or drill holes to drill pins in the bone, or a graphically navigated set of instructions for modifying the tissue. The data generated from the planning computer 114 may be transferred to the device computer 116 and/or tracking computer 119 through a wired or wireless connection in the operating room (OR); or transferred via a non-transient data storage medium (e.g., a compact disc (CD), a portable universal serial bus (USB) drive) if the planning computer 114 is located outside the OR. In particular embodiments, data (e.g., surgical plan data, image data, cut-files or others robotic instructions) is transferred in the OR using actuated LEDs as described in U.S. Pat. Pub. No. 20170245945 assigned to the assignee of the present application.

The device computer 116 in some inventive embodiments is housed in the moveable base 108 and contains hardware (e.g., controllers), software, data and utilities that are preferably dedicated to the operation of the surgical robot 102. This may include surgical device control, robotic manipulator control, the processing of kinematic and inverse kinematic data, the execution of registration algorithms, the execution of calibration routines, the execution of surgical plan data, coordinate transformation processing, providing workflow instructions to a user, utilizing position and orientation (POSE) data from the tracking system 106, and reading data received from the mechanical digitizer 118. The device computer 116 may further include an environmental map generator software module for generating an environmental map during the procedure as further described below. The environmental map generator software module may include a motion planner software module for dynamically planning a recovery path for the end-effector tool 115 in the event a user displaces the tool 115 during the procedure as further described below.

The optional tracking system 106 of the surgical system 100 includes two or more optical receivers 130 to detect the position of fiducial markers (e.g., retroreflective spheres, active light emitting diodes (LEDs)) uniquely arranged on rigid bodies. In still other embodiments the optical receivers are 3D laser scanners. The fiducial markers arranged on a rigid body are collectively referred to as a fiducial marker array 132, where each fiducial marker array 132 has a unique arrangement of fiducial markers, or a unique transmitting wavelength/frequency if the markers are active LEDs. In an embodiment, the fiducial markers are directly integrated onto or with the surgical device. An example of an optical tracking system is described in U.S. Pat. No. 6,061,644. The tracking system 106 may be built into a surgical light, located on a boom, a stand 140, or built into the walls or ceilings of the OR. The tracking system computer 136 may include tracking hardware, software, data and utilities to determine the POSE of objects (e.g., bones B, surgical robot 102) in a local or global coordinate frame. The POSE of the objects is collectively referred to herein as POSE data, where this POSE data may be communicated to the device computer 116 through a wired or wireless connection. Alternatively, the device computer 116 may determine the POSE data using the position of the fiducial markers detected from the optical receivers 130 directly.

The POSE data is determined using the position data detected from the optical receivers 130 and operations/processes such as image processing, image filtering, triangulation algorithms, geometric relationship processing, registration algorithms, calibration algorithms, and coordinate transformation processing. For example, the POSE of a digitizer probe 138 with an attached probe fiducial marker array 132b may be calibrated such that the probe tip is continuously known in physical space as described in U.S. Pat. No. 7,043,961. The POSE of the tool 115 may be known with respect to a device fiducial marker array 132a using a calibration method as described in U.S. Prov. Pat. App. 62/128,857. It should be appreciated, that the device fiducial marker 132a is depicted on the manipulator arm 110; however, the marker 132a may be positioned on the base 108 or the end-effector assembly 111. Registration algorithms may be executed to determine the POSE and coordinate transforms between a bone B, a fiducial marker array 132c or 132d, a surgical plan, and the surgical robot 102 using the aforementioned registration methods.

While 3D laser scanning has been contemplated as an adjunct to surgery (Harmon, L., et al. "3D laser scanning for image-guided neurosurgery." *Ann Arbor* 1001 (1994): 48113-4001), this technique has been met with limited success owing to the inadequate resolution of such scans that are nonetheless rapidly collected. This is known synonymously as light detection and ranging (LIDAR). Such 3D laser scanning is operative herein to detect a rapid and independent mapping of the surgical field for obstacles about which the surgical robotic system lacks information. The resulting scans are readily communicated and compared to the bone and/or fiducial marker registration to avoid collisions.

The POSE data is used by the computing system 104 during the procedure to update the POSE and/or coordinate transforms of the bone B, the surgical plan, and the surgical robot 102 as the manipulator arm 110 and/or bone B move during the procedure, such that the surgical robot 102 can accurately execute the surgical plan. In another embodiment, the surgical system 100 does not include a tracking system 106, but instead employs a bone fixation and monitoring system that fixes the bone directly to the surgical robot 102 and monitors bone movement as described in U.S. Pat. No. 5,086,401.

Figure 3:
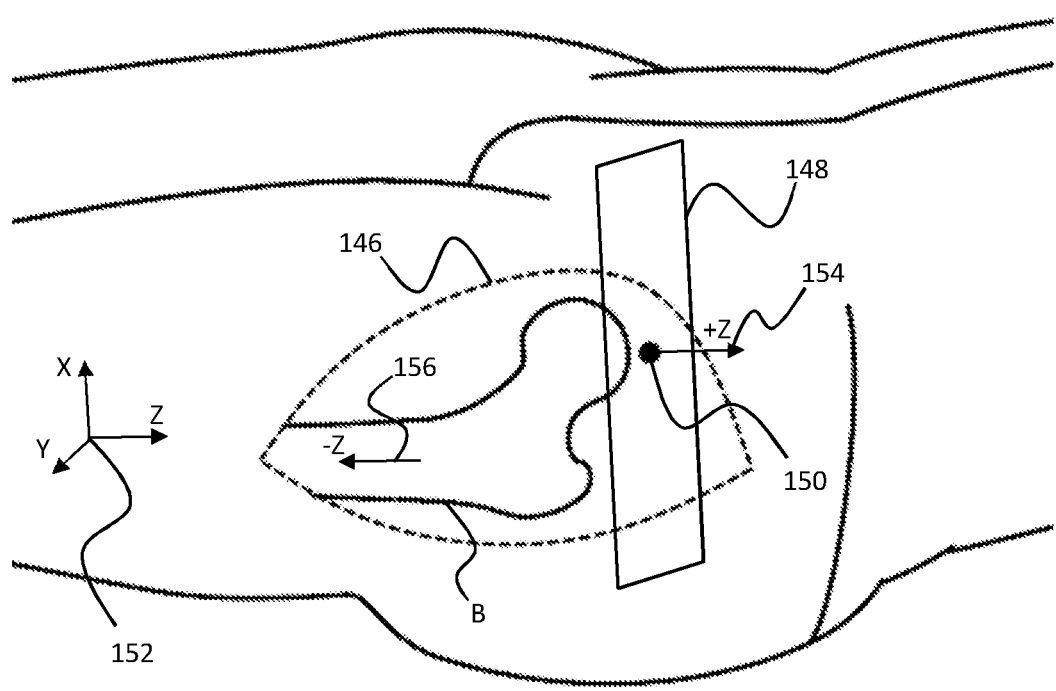
FIG. 3 depicts an exposed proximal femur and a boundary used to dynamically generate an environmental map in accordance with embodiments of the invention.

With reference to FIG. 3, a particular inventive embodiment of a method for dynamically generating an environmental map is shown. The surgical team first exposes the bone B via an incision 146, and the bone B is registered to the surgical robot 102 and the surgical plan (the surgical plan having the tool path 10) with techniques known in the art. After registration, a boundary 148 (e.g., a hyperplane, a meshed surface generated by a camera) is defined in space (e.g., in a coordinate system associated with the surgical robot 102 or tracking system 106) as: a) the highest point 150 on the bone B, plus some optional offset; and b) parallel to an X-Y plane that is defined perpendicular to a longitudinal axis of the bone B as further described. The algorithms for such registration and by extension robotic navigation are well known as provided in exemplary form in Bobrow, J. E. et al. "Time-optimal control of robotic manipulators along specified paths." Int. J. Robot. Res., 4(3):3-17, 1985. The highest point on the bone may be determined by designating such point as a landmark on a 3-D virtual bone model of the bone B in the pre-operative planning software, wherein once registered to the actual bone is known in physical space. In specific embodiments, the 'high point' refers to the most proximal end point or the most distal end point on the bone depending on which end the surgical robot 102 is operating (e.g., if the surgical robot 102 is preparing the proximal femur, then the 'high point' is the most proximal end point of the femur). The X-Y plane may be defined relative to the bone B using several methods. In a specific embodiment, a coordinate system 152 of the bone B is defined relative to a 3-D virtual bone model of the bone B in the pre-operative planning software. Generally, a +Z-axis 154 and −Z-axis 156 of the bone B is defined along a longitudinal axis of the bone B, such as the mechanical axis or anatomical axis of the bone B. The X-axis and Y-axis are then defined perpendicular to the Z-axis and perpendicular to one another using anatomical landmarks (e.g., femoral condyles). Here, as illustrated in FIG. 3, the +Z-axis 154 is shown pointing away from the bone B and the −Z-axis is shown pointing towards the bone B. In other words, the +Z-axis 154 is shown pointing in a direction opposing the direction of the end-effector's tool path 10, and the −Z-axis 156 is shown pointing in a direction towards the end-effector's tool path 10. The highest point 150 is defined as the most +Z point on the bone B as determined from the digitizing and registration process, plus some optional offset. The boundary 148 is then defined in space using the highest point 150 and the X-Y plane as defined above.

The boundary 148 may be defined by the computing system 104 and stored in the environmental map generator software module. The environmental map generator then begins mapping the environment by designating anything beyond the boundary 148 in the +Z-axis direction as free space FS and anything below the surface in the −Z-axis direction as invalid space IS. The free space FS is defined as any region in the environment where the end-effector can safely travel, while the invalid space IS is defined as any region in the environment that may be unsafe and/or cause an unintended collision with the end-effector tool.

Figure 4A:
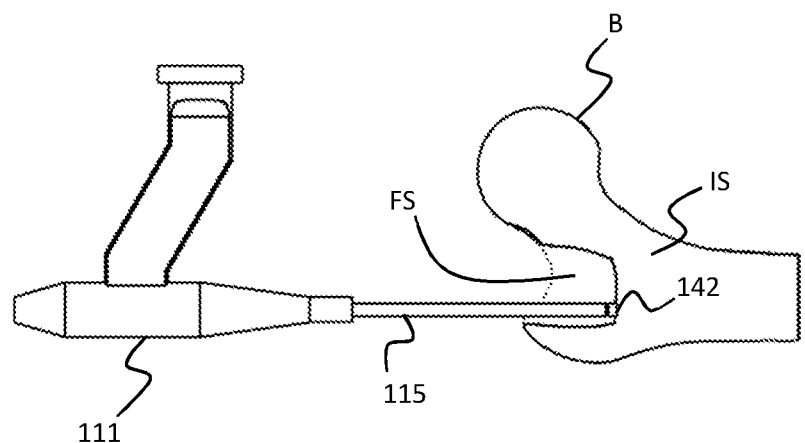
FIGS. 4A-4C depicts the progression of a method for dynamically generating an environmental map and planning a recovery tool path in accordance with embodiments of the invention, where
Figure 4B:
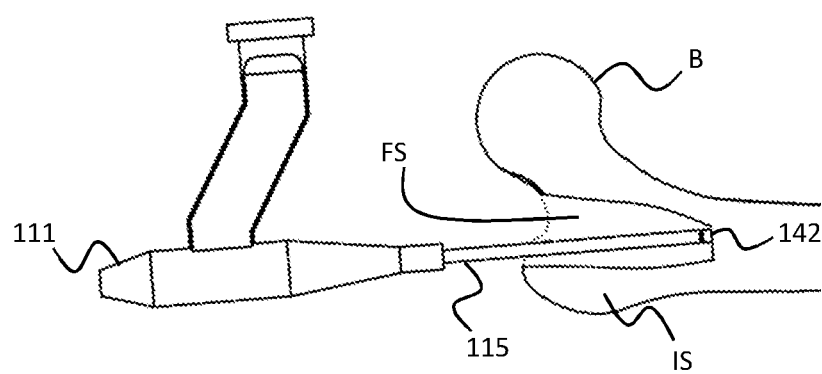
Figure 4C:
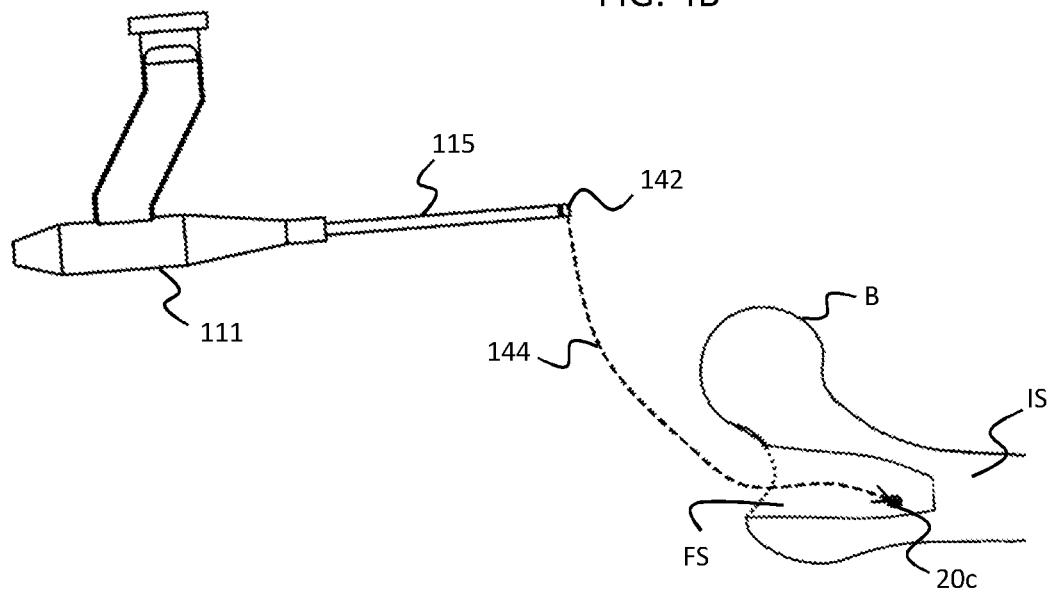

With reference to FIGS. 4A-4C, particular embodiments for furthering the generation of the environmental map as the end-effector tool removes bone is shown. FIGS. 4A-4C depicts the end-effector assembly 111 operating a tool 115 having a tool tip 142 at different stages throughout embodiments of the inventive method. FIG. 4A depicts the end-effector tool 115 removing material from a bone B. The manipulator arm 110 manipulates the end-effector tool 115 according to a tool path 10 registered to the bone B. As the end-effector tool 115 removes bone B, the environmental map generator associated with at least one of the device computer 116 or tracking computer 119 maps the environment in real-time. The environmental map generator maps the environment by labeling the volume of removed material by the end-effector tool 115 as free space FS, and all other regions as invalid space IS. FIG. 4B depicts the end-effector tool 115 positioned farther along the tool path 10. As such, the volume of the free space FS has increased as the end-effector tool 115 has removed more bone B. Therefore, the environmental map is generated and updated in real-time based on the movements of the end-effector tool 115 as the tool 115 removes bone B. The environmental map generator knows the POSE of the tool 115 as the tool 115 is removing bone B to update the free space FS based on at least one of: the kinematics of the robot manipulator arm, POSE data collected from a tracking system, or a combination thereof. In particular inventive embodiments, the environmental map generator only updates the environmental map (i.e., free space FS and invalid space IS) when the end-effector tool 115 is 'on' (e.g., an end-mill actively spinning) and when the end-effector tool 115 has crossed over the boundary 148 from +Z to −Z. Therefore, the motion planner module does not inadvertently mislabel a region of the environment as free space FS.

In the event of bone motion at any moment during the procedure, the POSE of the surgical plan having the tool path 10 and the environmental map are updated to maintain their relative POSE to the bone B. If a tracking system 106 is present, the POSEs may be updated in real-time based on the POSE data. If the surgical system utilizes a fixation system, bone motion monitoring system, and recovery markers as described in U.S. Pat. No. 5,086,401 and U.S. Pat. No. 6,430,434, then the recovery markers are used to update the relative POSEs. Therefore, the labeled free space FS and labeled invalid space IS in the environmental map is not compromised in the event of bone motion.

Planning a Recovery Tool Path

With reference still to FIGS. 4A to 4C, particular embodiments of a method for dynamically planning a recovery tool path with the environmental map is also shown. FIG. 4B depicts the end-effector tool 115 at point in the tool path 10 where the procedure is paused due to one of several reasons, such as a safety reason. As shown in FIG. 4C, a user then displaces the end-effector tool 115 to a displaced position away from the tool path 10. FIG. 4C depicts the tool 115 being displaced outside of the volume of removed bone B. Once the user is ready to resume the procedure, the motion planner module searches for a recovery tool path 144 based on the environmental map (i.e., free space FS and invalid space IS). More specifically, the motion planner module searches for a recovery tool path 144 that: a) minimizes the path length from the current displaced position of the tool 115 (as shown in FIG. 4C) back to, or near, the pre-displaced position of the tool 115 on the tool path 10 (as shown in FIG. 4B); and b) maximizes dexterity and distance away from obstacles (i.e., invalid space IS). The motion planner module may utilize one or more algorithms to search for the recovery tool path 144 based on the foregoing constraints (a) and (b). The algorithms illustratively include optimization algorithms, probability roadmaps (PRM), rapidly-exploring random trees (RRT), potential field method, or any variants of the mentioned algorithms. The motion planner module may further use existing landmarks such as checkpoints 20C in the tool path 10 to navigate the end-effector tool 115 back to, or near, the pre-displaced position of the end-effector tool 115. More specifically, if the tool path 10 for the end-effector tool 115 includes checkpoints (20*a*, 20*b*, 20*c*, 20*d*), then each checkpoint (20*a*, 20*b*, 20*c*, 20*d*) encountered while removing the bone B is checked for reachability. A reachable checkpoint is any checkpoint in the robot workspace that can be reached by the robot's end-effector since not all of the checkpoints in the cut-file may be directly on the end-effector's tool path 10. Reachable checkpoints are recorded and labeled as valid points to be used as vertexes during recovery path planning. The end-effector tool 115 then travels along the recovery tool path 144 back to, or near, the pre-displaced position to resume the removal of bone B.

Visual Feedback

During milling, the graphical user interface may display the progress of the end-effector removing bone. The GUI may display the 3-D bone model being milled. To better display the progression of the milling, the GUI may also display the amount of bone removed based on the labelled free space. Since the software module is recording and labelling the removed bone in real-time as free space, the free space is used as a metric to update the volume of bone removed accordingly. This provides a quick method to determine and display the progression of the milling in real-time relative to a virtual representation of the bone.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method to dynamically generate an environmental map in a robotic assisted surgery system, comprising:
   removing material from a workpiece or a bone by manipulating an end-effector tool of the robotic surgical system along a tool path; and
   dynamically generating the environmental map as material is being removed by labeling the removed material as free space in the environmental map and labeling the non-removed material as invalid space in the environmental map.

2. The method of claim 1 further comprising generating a three-dimensional virtual model of the bone and registering the virtual model of the bone to the bone.

3. The method of claim 1 wherein the labelling of the removed material as free space in the environmental map only occurs when an end-effector tool of the robotic assisted surgical system is in an 'on' operating state.

4. The method of claim 3 wherein the labelling of the removed material as free space in the environmental map only occurs when the end-effector tool crosses a boundary in a direction towards the bone.

5. The method of claim 1 wherein the environmental map is generated with reference to a robotic coordinate system or a tracking system coordinate system.

6. The method of claim 1 wherein the longitudinal axis of the bone is at least one of a mechanical axis of the bone or an anatomical axis of the bone.

7. The method of claim 1 further comprising planning a recovery tool path for an end-effector tool with the dynamically generated environmental map.

8. The method of claim 7 wherein the planning of the recovery tool path further comprises displacing the end-effector tool away from the tool path to a displaced position and planning the recovery tool path based on the labelled free space and the labelled invalid space.

9. The method of claim 8 wherein the planning of the recovery tool path further comprises minimizing a path length from the displaced position into proximity to the pre-displaced position on the tool path utilizing the labeled free space, and maximizing dexterity and distance away from obstacles utilizing the labeled invalid space.

10. The method of claim 9 wherein the minimizing of the path length and the maximizing of the dexterity and distance away from obstacles is accomplished with an algorithm including at least one of: optimization algorithms, probability roadmaps (PRM), rapidly-exploring random trees (RRT), or potential field methods.

11. The method of claim 10 wherein the tool path further includes one or more checkpoints positioned along the tool path wherein the planning of the recovery tool path from the displaced position back to, or near, the pre-displaced position utilizes one or more of the checkpoints.

12. The method of claim 11 further comprising determining which of the one or more checkpoints is in closest proximity to the pre-displaced position of the end-effector tool and planning the recovery tool path based on one or more of said checkpoints.

13. A surgical system comprising:
    a surgical robot with an end effector tool; and
    a computing system comprising a processor and software to generate the environmental map of claim 1.

14. The system of claim 13 further comprising an environmental map generator software module for generating an environmental map.

15. The system of claim 14 wherein the environmental map generator software module further comprises a motion planner software module for dynamically planning a recovery path for the end-effector tool.

16. The system of claim of claim 13 further comprising at least one of a mechanical digitizer or a non-mechanical tracking system.

17. The method of claim 1 further comprising registering the bone relative to the robotic assisted surgical system.

18. The method of claim 1 further comprising defining a boundary in the environmental map based a plane non-parallel to a longitudinal axis of the bone.

19. The method of claim 18 further comprising:
    labeling regions starting at the boundary and away from the bone as free space in the environmental map; and
    labeling regions starting at the boundary and towards the bone as invalid space in the environmental map.

* * * * *